United States Patent [19]
Laby

[11] Patent Number: 4,623,345
[45] Date of Patent: Nov. 18, 1986

[54] CAPSULE FOR ADMINISTRATION TO RUMINANTS

[76] Inventor: Ralph H. Laby, 52 Bryson Street, Canterbury, Victoria, Australia

[21] Appl. No.: 601,213

[22] Filed: Apr. 17, 1984

[30] Foreign Application Priority Data

Apr. 22, 1983 [AU] Australia .................. PF 9026/83

[51] Int. Cl.⁴ ............................................. A61M 31/00
[52] U.S. Cl. ........................................ 604/892; 604/93
[58] Field of Search ........................ 604/890, 896, 93

[56] References Cited
U.S. PATENT DOCUMENTS
3,844,285 10/1974 Laby .................................. 604/892

Primary Examiner—Sherri E. Vinyard
Attorney, Agent, or Firm—Bacon and Thomas

[57] ABSTRACT

A capsule for administration to a ruminant, comprises two body portions of magnesium or an alloy thereof, pivotally connected for movement between a relatively small cross-sectional configuration in which the capsule can be administered per os into the rumen, and a relatively larger cross-sectional configuration adopted within the rumen to resist regurgitation. The pivotal connection between the body portions is provided by a resiliently flexible material such as rubber or silicone made electrically conductive by means of a matrix of conductive particles, for example carbon particles. The flexible material at least partially covers a surface of each body portion. When the capsule is in the rumen the conductive particles act as a cathode and the body portions as anodes.

11 Claims, 4 Drawing Figures

CAPSULE FOR ADMINISTRATION TO RUMINANTS

BACKGROUND OF THE INVENTION

1. Field of the Invention

The present invention relates to a capsule for administration to ruminants for the prevention or treatment of disorders particularly hypomagnesemia and grass tetany.

2. Description of the Prior Art

There is described in our Australian Patent Specification No. 470,538 and a capsule which is adapted to be administered per os to pass into the rumen to supplement the magnesium intake of the ruminant for the purpose of combating grass tetany, the disorder arising from magnesium deficiency.

Briefly, the capsule described in the above patent specification comprises a pair of semi-cylinders composed of magnesium or an alloy thereof. The interior of each of the semi-cylinders is covered by a coating of a resiliently flexible electrically insulating material which is so formed as to provide a hinge which links the two semi-cylinders. The two cylinders are thus pivotal from a closed condition in which they define a closed cylinder which can be administered per os, to an open position which they assume in the reticulo-rumen (rumen). The interior of each semi-cylinder houses a metal, for example, steel wool, which is lower in the electrochemical series than magnesium and which is electrically connected by means of screws or rivets to the magnesium or magnesium alloy which forms the body of the semi-cylinder. When the other metal is immersed in the contents of the rumen, the other metal acts as a cathode and the electrolytic effect thus created provides a high dissolution rate for the magnesium or alloy. Further details of this previously proposed capsule may be obtained from the above patent specifications.

Although this previously proposed capsule is effective in operation, it is relatively expensive to produce in that it requires a separate cathode plus means for attaching, and electrically connecting, the cathode to the body of the semi-cylinder. Commercially, capsules for the treatment of magnesium deficiencies in ruminants are highly cost-sensitive and a requirement exists for a capsule which can be produced more cheaply.

SUMMARY OF THE INVENTION

According to the present invention, there is provided a capsule for administration to a ruminant, comprising two body portions consisting of, or containing, magnesium or an alloy thereof, and hinge means pivotally connecting the body portions for pivotal movement between a relatively small cross-sectional configuration in which the capsule can be administered per os into the rumen, and a relatively larger cross-sectional configuration adopted within the rumen to resist regurgitation, said hinge means comprising a flexible material made electrically conductive by means of a matrix of conductive particles, the arrangement being such that when the capsule is in the rumen the conductive particles act as a cathode and the body portions as anodes.

Further according to the present invention, there is provided a capsule for administration to a ruminant, comprising two body portions consisting of, or containing, magnesium or an alloy thereof, and hinge means pivotally connecting the body portions for pivotal movement between a closed configuration in which the capsule can be administered per os into the rumen, and an open configuration adopted within the rumen to resist regurgitation, said hinge means comprising a flexible material made electrically conductive by means of a matrix of conductive particles, said material being bonded to the body portions by means of an electrically insulating layer, and means providing an electrical connection between the flexible material and the body portions, the arrangement being such that the conductive particles act as a cathode when the capsule is within the rumen, and the body portions act as anodes.

Preferably, the material is resiliently flexible and is a carbon-containing rubber. The electrical connection between the material and the body portions is preferably made by removing or otherwise interrupting the bonding layer at a number of points.

BRIEF DESCRIPTION OF THE DRAWINGS

An embodiment of the invention will now be described, by way of example only, with reference to the accompanying diagrammatic drawings, in which.

DESCRIPTION OF THE PREFERRED EMBODIMENTS

Figure 1:
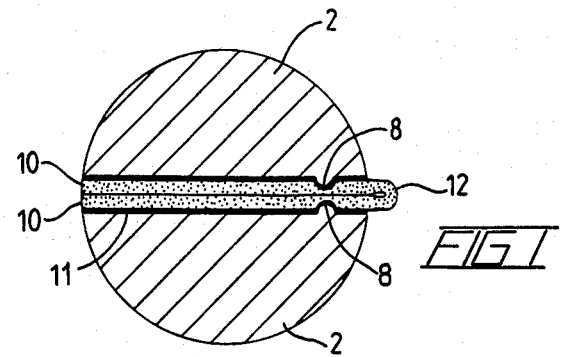
FIG. 1 is a cross-section of a capsule in accordance with a preferred embodiment of the invention, the capsule being shown in a closed configuration for administration per os.

The capsule shown in the drawings comprises two body portions 2 formed, for example by casting, from magnesium or an alloy thereof whereby the body portions consist of, or contain, magnesium. Each body portion is elongate and is of approximately semi-cylindrical form with a semi-hemispherical front end 4 and a flat rear end 6. When the two body portions are assembled together as shown in FIG. 1, they form a cylinder with a hemispherical front end which facilitates insertion of the capsule into the oesophagus of a ruminant. When used for cattle, the body portions 2 will be about 150 to 180 mm long and when placed together form a cylinder of a diameter of from 30 to 40 mm.

The flat diametral surface of each semi-cylindrical body portion 2 is formed with a longitudinally extending rectilinear rib 8. This surface carries a coating 10 of a resiliently flexible, electrically-conductive, rubber which is bonded to the surface by means of an electrically-insulating bonding material 11. It will be noted from FIGS. 1 and 2 that the coating 10 is of a greater thickness than the depth of the ribs 8 so that the ribs are covered by the coating 10 and, therefore, in the zone of the ribs 8 the coating 10 is of reduced thickness. Also, as shown in FIGS. 1 and 2, the coating 10 is so formed as to provide a hinge 12 which links the two body portions 2.

The body portions 2 are folded together to form the cylindrical configuration of FIG. 1 against the tension of the hinge 12. The capsule may be retained in this configuration by means of a band (not shown) of soluble material, for example a gelatin tape, or alternatively the constriction of the oesophagus in the animal may be sufficient to provide the necessary restraint during administration. Once in the reticulo rumen, the capsule opens to the configuration shown in FIG. 2 which resists regurgitation and which allows the contents of the rumen to contact the conductive rubber coatings 10.

Figure 2:
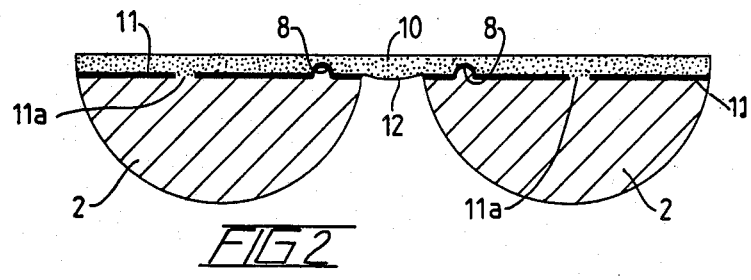
FIG. 2 is a cross-section, similar to FIG. 1, but showing the capsule in an open configuration which it adopts when in the rumen.
Figure 3:
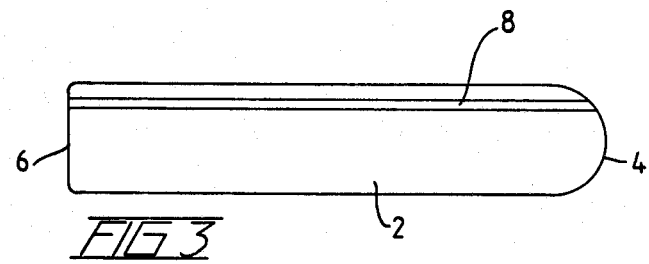
FIG. 3 is a plan view of a body portion of the capsule prior to the application of a flexible electrically-conductive coating.
Figure 4:
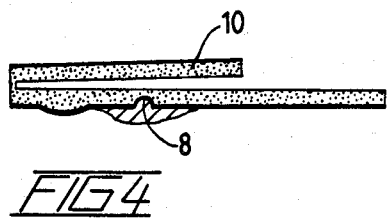
FIG. 4 is a cross-section showing the manner in which the coating can fold for regurgitation after dissolution of the body portions.

During manufacture of the capsule, electrical contact is provided between the conductive rubber coating 10 and each body portion 2 for example by rubbing away or otherwise interrupting the bonding material 11 at a number of points (typically two points for each body portion) one of which is shown schematically at 11a in FIG. 2. When in the rumen, the conductive material of the rubber acts as a cathode and the body portion acts as an anode which will corrode principally on its outer surface. Upon dissolution of substantially all of the magnesium (or alloy thereof), the coating 10 will remain and this will be regurgitated by the animal. The portions of reduced thickness defined in the coating 10 due to the presence of the longitudinal ribs 8 define zones about which the coating will tend to fold when the magnesium has corroded and this facilitates regurgitation of the coating. It has been found that the body portions will tend to corrode in a direction from their semi-circular outer surfaces towards the ribs and that, usually, one of the body portions will dissolve away completely before the other body portion. In this case, the coating will tend to fold as shown in FIG. 4 about a line defined at the site of the rib of the body portion which has completely dissolved; in FIG. 4 a small, and relatively insignificant, amount of the other body portion is shown remaining in the zone of its rib.

Preferably, the electrically-insulating bonding material 11 is a rubber-based bonding agent such as that sold under the trade mark "Chemlok" of Albright & Wilson Ltd.

Preferably, the conductive rubber is a carbon-containing rubber, with the carbon granules being mixed in a manner which maintains good electrical contact between the granules. Instead of using carbon granules, the rubber can be made conductive by means of granules or powder of a metal which is lower than magnesium in the electrochemical series, for example zinc, iron, copper, nickel, or cobalt. Instead of using rubber as a resiliently, flexible material in which a matrix of conductive particles is held, other biologically-acceptable materials such as silicone, polyurethane, or plasticized polyvinylchloride may be used.

The preferred coating material is, however, carbon-containing conductive rubber and the fact that this will act as a cathode will be demonstrated by the following examples.

EXAMPLE I

Capsules were prepared by bonding 3 grades of rubber to magnesium alloy (AZ 91- German Standard casting alloy having approximately 9% aluminium 0.3-1.0% zinc) solid semi-cylinders. Duplicates were made.

Three grades of rubber were:—
(a) Insulating—no carbon black, filled with $Fe_2O_3$
(b) High resistance—40% carbon black
(c) Low resistance (i.e. conductive)—40% carbon black, mixed in a manner that maintains good contact between carbon granules; this requires less mixing than is usual to produce a high resistance rubber.

The semi-cylinders were 100 mm long and 25 mm diameter semi-cylinders, the rubber being glued to the flat face of the semi-cylinders using a rubber cement. The cement layer was electrically insulating, and electrical contact was achieved between rubber and semi-cylinder by inserting two self-tapping steel screws, one at each end of each semi-cylinder and 80 mm apart. The heads of all screws were then covered with an electrically insulating film.

The electrical resistance between point contacts, one on the rubber surface midway between the screws, the other on the cylindrical surface of the anode was measured (see table below).

In vivo loss of magnesium from alloy anodes was determined from weight loss measurements after 15 days in the rumen of fistulated cattle (see Table 1 below).

TABLE I
Electrical resistance and anode weight loss of devices prepared from rubbers of differing resistance

| Rubber | Resistance, Ω | Mean Weight Loss, mg d$^{-1}$ (over 15 days) |
|---|---|---|
| Insulating | >1 million | 330 |
| High resistance | ≅55,000 | 335 |
| Low resistance | 65-75 | 504 |

It will be seen that the low resistance (that is, conductive) rubber gave release rates approximately 50% faster than either the insulating or high resistance rubber capsules, and this indicates that the carbon dispersed in conductive rubber does act as a suitable cathode for controlling release rate.

EXAMPLE II

In a further trial, commercial prototype magnesium alloy semi-cylinders (160×30 mm) were bonded to rubber to form two groups of two-anode cylindrical magnesium capsules which open in the rumen as described previously, in order to prevent regurgitation. To ensure good electrical contact between rubber and anode, steel screws were inserted through the rubber 25 mm from each end of both anodes (four per capsule). In one group of capsules, the rubber was an insulating black rubber, the resistance as measured between the anodes of the completed capsules being >10$^6$Ω, while in the other group, the rubber was a conducting rubber (containing carbon black), the resistance as measured between the anodes of the completed capsules being from 30 to 140Ω.

Two groups of rumen fistulated steers grazing an improved green pasture were dosed with the above capsules. The capsules were removed at approximately 5 day intervals over a 106 day trial period, washed in 95% ethanol, dried and weighed to determine mean daily release rates of magnesium. The results are given in Table II below.

TABLE II
Magnesium release g d$^{-1}$ from commercial prototypes capsules bonded with (a) an insulating and (b) a conducting rubber.

| Magnesium Release g d$^{-1}$ | |
|---|---|
| (a) Insulating rubber (>10$^6$ Ω) 13 animals | (b) conducting rubber (30 to 140 Ω) 10 animals |
| 1.570 | 1.939 |

TABLE II-continued

Magnesium release g d$^{-1}$ from commercial prototypes capsules bonded with (a) an insulating and (b) a conducting rubber.

| Magnesium Release g d$^{-1}$ | |
|---|---|
| (a) Insulating rubber (>10$^6$ Ω) 13 animals | (b) conducting rubber (30 to 140 Ω) 10 animals |
| 1.484 | 2.033 |
| 1.386 | 1.749 |
| 1.319 | 1.852 |
| 1.197 | 1.723 |
| 1.472 | 1.719 |
| 1.491 | 1.715 |
| 1.625 | 1.779 |
| 1.378 | 1.822 |
| 1.354 | 1.755 |
| 1.476 | mean = 1.809 |
| 1.276 | S.D. 0.1058 |
| 1.178 | |
| mean = 1.400 | |
| S.D. 0.1357 | |

The conducting rubber cathodes, where the anode-to-anode resistance was >140 ohm, thus lead to a 29% increase in magnesium release rate from 1.40 g d$^{-1}$ to 1.81 g d$^{-1}$ relative to the capsules bonded with insulating rubber. This increase was significant (P<0.001).

The capsule described herein thus differs from the previously proposed capsule described in patent No. 470,538 in that the cathode is formed by a flexible conductive layer which is used to coat the semi-cylinders to provide a hinge between the two cylinders, a separate metal cathode not being required. Conductive rubbers, which are the preferred materials for the layer, are well know per se and are readily available and the capsule can be produced relatively inexpensively. The release rate of the magnesium can also be readily controlled by varying the resistance of the rubber and/or by varying the area of the rubber which has direct exposure to the rumen content by only partially covering the diametral surface of the body portion with the rubber.

The embodiment has been described by way of example only and modifications are possible within the scope of the invention which includes every novel feature or combination of features disclosed.

What is claimed is:

1. A capsule for administration to a ruminant, comprising two body portions comprising magnesium or an alloy thereof, and hinge means pivotally connecting the body portions for pivotal movement between a relatively small cross-sectional configuration in which the capsule can be administered per os into the rumen, and a relatively larger cross-sectional configuration adopted within the rumen to resist regurgitation, said hinge means comprising a flexible material made electrically conductive by means of a matrix of conductive particles, the arrangement being such that when the capsule is in the rumen the conductive particles act as a cathode and the body portions as anodes.

2. A capsule according to claim 1, wherein the flexible material is resiliently flexible such that the body portions are biased to open about said hinge means into said relatively larger cross-sectional configuration.

3. A capsule according to claim 2, wherein the flexible material is selected from the group consisting of rubber, silicone, polyurethane, and plasticized polyvinylchloride.

4. A capsule according to claim 3, wherein the conductive particles are selected from the group consisting of carbon or a metal lower than magnesium in the electrochemical series.

5. A capsule according to claim 1, wherein the flexible material defines a layer at least partially covering a surface of each body portion.

6. A capsule according to claim 5, wherein each said body portion includes a substantially rectilinear rib projecting from said surface, the layer covering said surface to a thickness exceeding the depth of the rib, the layer being of reduced thickness in the zone of the rib whereby to define a line about which the layer will tend to fold after the body portions have substantially completely dissolved in the rumen so as to facilitate regurgitation of the said layer.

7. A capsule for administration to a ruminant, comprising two body portions comprising magnesium or an alloy thereof, and hinge means pivotally connecting the body portions for pivotal movement between a closed configuration in which the capsule can be administered per os into the rumen, and an open configuration adopted within the rumen to resist regurgitation, said hinge means comprising a flexible material made electrically conductive by means of a matrix of conductive particles, an electrically insulating layer bonding said material to the body portions, and means providing an electrical connection between the flexible material and the body portions, the arrangement being such that the conductive particles act as a cathode when the capsule is within the rumen, and the body portions act as anodes.

8. A capsule according to claim 7, wherein the electrical connection is provided between the flexible material and the body portions by interrupting the insulating bonding layer at a number of points.

9. A capsule according to claim 7, wherein each body portion is in the form of a solid semi-cylinder whereby the capsule is substantially cylindrical in the closed configuration, each semi-cylindrical body portion having a diametral surface, said flexible material being bonded to the diametral surface of each body portion.

10. A capsule according to claim 9, wherein the flexible material comprises a carbon-containing rubber, said material resiliently biasing the body portions to the open configuration.

11. A capsule according to claim 9, wherein each body portion includes a longitudinal rib projecting from its diametral surface to define in the flexible material a zone of reduced thickness about which the material will tend to fold after the body portions have substantially completely dissolved within the rumen so as to facilitate regurgitation of the said layer.

* * * * *